(12) United States Patent
Bohn et al.

(10) Patent No.: US 10,543,116 B2
(45) Date of Patent: Jan. 28, 2020

(54) BALLOON EXPANDABLE ENDOPROSTHESIS

(71) Applicant: W. L. Gore & Associates, Inc., Newark, DE (US)

(72) Inventors: Jane K. Bohn, Flagstaff, AZ (US); Cody L. Hartman, Flagstaff, AZ (US); Deenu G. Kanjickal, Flagstaff, AZ (US); Bret J. Kilgrow, Flagstaff, AZ (US); Joseph B. Koenig, Flagstaff, AZ (US); James J. Nickerson, Flagstaff, AZ (US); Thomas G. Triebes, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 203 days.

(21) Appl. No.: 15/531,252

(22) PCT Filed: Nov. 25, 2015

(86) PCT No.: PCT/US2015/062799
§ 371 (c)(1),
(2) Date: May 26, 2017

(87) PCT Pub. No.: WO2016/086202
PCT Pub. Date: Jun. 2, 2016

(65) Prior Publication Data
US 2018/0296377 A1 Oct. 18, 2018

Related U.S. Application Data

(63) Continuation of application No. 14/950,165, filed on Nov. 24, 2015.
(Continued)

(51) Int. Cl.
*A61F 2/958* (2013.01)
*A61F 2/07* (2013.01)
(Continued)

(52) U.S. Cl.
CPC .......... *A61F 2/958* (2013.01); *A61F 2/07* (2013.01); *A61M 25/10* (2013.01); *A61F 2/89* (2013.01);
(Continued)

(58) Field of Classification Search
CPC ...... A61F 2/06; A61F 2/07; A61F 2/82; A61F 2/86; A61F 2/95; A61F 2/954;
(Continued)

(56) References Cited

U.S. PATENT DOCUMENTS 4,503,569 A    3/1985  Dotter
4,655,771 A    4/1987  Wallsten
(Continued)

FOREIGN PATENT DOCUMENTS

CN    103702709 A    4/2014
CN    103930157 A    7/2014
(Continued)

OTHER PUBLICATIONS

European Search Report issued in EP Application No. 00311543.3, completed Oct. 31, 2002, 6 pages.
(Continued)

*Primary Examiner* — Ryan J. Severson (57) ABSTRACT

An improved medical device reduces the loss of longitudinal length during expansion of a stent-graft from a compressed state to an expanded state. For example, the stent-graft is placed over a cover that provides resistance to expansion of the balloon during inflation, which reduces longitudinal compressing forces exerted on the stent-graft.

23 Claims, 6 Drawing Sheets

Related U.S. Application Data (60) Provisional application No. 62/085,066, filed on Nov. 26, 2014.

(51) Int. Cl.
*A61M 25/10* (2013.01)
*A61F 2/89* (2013.01)

(52) U.S. Cl.
CPC ... *A61F 2002/072* (2013.01); *A61F 2240/001* (2013.01); *A61F 2240/008* (2013.01); *A61M 2025/1004* (2013.01); *A61M 2025/1068* (2013.01); *A61M 2025/1075* (2013.01); *A61M 2025/1084* (2013.01)

(58) Field of Classification Search
CPC .......... A61F 2/958; A61F 2/962; A61F 2/966; A61F 2002/072; A61F 2002/9522; A61F 2002/9583; A61M 25/10; A61M 2025/1059; A61M 2025/1075; A61M 2025/1081; A61M 2025/1084
See application file for complete search history.

(56) References Cited

U.S. PATENT DOCUMENTS

| | | |
|---|---|---|
| 4,739,762 A | 4/1988 | Palmaz |
| 4,776,337 A | 10/1988 | Palmaz |
| 5,019,090 A | 5/1991 | Pinchuk |
| 5,037,427 A | 8/1991 | Harada et al. |
| 5,061,275 A | 10/1991 | Wallsten et al. |
| 5,102,417 A | 4/1992 | Palmaz |
| 5,104,404 A | 4/1992 | Wolff |
| 5,122,154 A | 6/1992 | Rhodes |
| 5,123,917 A | 6/1992 | Lee |
| 5,201,757 A | 4/1993 | Heyn et al. |
| 5,236,447 A | 8/1993 | Kubo et al. |
| 5,282,824 A | 2/1994 | Gianturco |
| 5,300,500 A | 4/1994 | Lee et al. |
| 5,314,472 A | 5/1994 | Fontaine |
| 5,330,500 A | 7/1994 | Song |
| 5,360,443 A | 11/1994 | Barone et al. |
| 5,405,377 A | 4/1995 | Cragg |
| 5,443,495 A | 8/1995 | Buscemi et al. |
| 5,443,496 A | 8/1995 | Schwartz et al. |
| 5,443,499 A | 8/1995 | Schmitt |
| 5,449,373 A | 9/1995 | Pinchasik et al. |
| 5,507,767 A | 4/1996 | Maeda et al. |
| 5,507,771 A | 4/1996 | Gianturco |
| 5,549,663 A | 8/1996 | Cottone et al. |
| 5,575,816 A | 11/1996 | Rudnick et al. |
| 5,591,195 A | 1/1997 | Taheri et al. |
| 5,662,703 A | 9/1997 | Yurek et al. |
| 5,665,115 A | 9/1997 | Cragg |
| 5,674,241 A | 10/1997 | Bley et al. |
| 5,683,448 A | 11/1997 | Cragg |
| 5,693,086 A | 12/1997 | Goicoechea et al. |
| 5,708,044 A | 1/1998 | Branca |
| 5,725,570 A | 3/1998 | Heath |
| 5,728,150 A | 3/1998 | McDonald et al. |
| 5,735,892 A | 4/1998 | Myers et al. |
| 5,749,852 A | 5/1998 | Schwab et al. |
| 5,755,774 A | 5/1998 | Pinchuk |
| 5,756,553 A | 5/1998 | Iguchi et al. |
| 5,769,884 A | 6/1998 | Solovay |
| 5,769,887 A | 6/1998 | Brown et al. |
| 5,800,456 A | 9/1998 | Maeda et al. |
| 5,800,515 A | 9/1998 | Nadal et al. |
| 5,800,521 A | 9/1998 | Orth |
| 5,814,063 A | 9/1998 | Freitag |
| 5,824,043 A | 10/1998 | Cottone, Jr. |
| 5,824,059 A | 10/1998 | Wijay |
| 5,843,161 A | 12/1998 | Solovay |
| 5,873,906 A | 2/1999 | Lau et al. |
| 5,876,432 A | 3/1999 | Lau et al. |
| 5,879,369 A | 3/1999 | Ishida |
| 5,891,193 A | 4/1999 | Robinson et al. |
| 5,899,934 A | 5/1999 | Amundson et al. |
| 5,906,639 A | 5/1999 | Rudnick et al. |
| 5,919,225 A | 7/1999 | Lau et al. |
| 5,922,020 A | 7/1999 | Klein et al. |
| 5,968,091 A | 10/1999 | Pinchuk et al. |
| 5,984,957 A | 11/1999 | Laptewicz, Jr. et al. |
| 6,001,125 A | 12/1999 | Golds et al. |
| 6,004,348 A | 12/1999 | Banas et al. |
| 6,007,545 A | 12/1999 | Venturelli |
| 6,013,854 A | 1/2000 | Moriuchi |
| 6,015,432 A | 1/2000 | Rakos et al. |
| 6,016,846 A | 1/2000 | Knittel et al. |
| 6,022,359 A | 2/2000 | Frantzen |
| 6,022,374 A | 2/2000 | Imran |
| 6,048,360 A | 4/2000 | Khosravi et al. |
| 6,071,307 A | 6/2000 | Rhee et al. |
| 6,077,296 A | 6/2000 | Shokoohi et al. |
| 6,107,004 A | 8/2000 | Donadio et al. |
| 6,123,712 A | 9/2000 | Di Caprio et al. |
| 6,139,573 A | 10/2000 | Sogard et al. |
| 6,139,575 A | 10/2000 | Shu et al. |
| 6,143,022 A | 11/2000 | Shull et al. |
| 6,146,417 A | 11/2000 | Ischinger |
| 6,159,239 A | 12/2000 | Greenhalgh |
| 6,165,210 A | 12/2000 | Lau et al. |
| 6,171,334 B1 | 1/2001 | Cox |
| 6,174,328 B1 | 1/2001 | Cragg |
| 6,217,609 B1 | 4/2001 | Haverkost |
| 6,231,597 B1 | 5/2001 | Deem et al. |
| 6,264,687 B1 | 7/2001 | Tomonto |
| 6,283,992 B1 | 9/2001 | Hankh et al. |
| 6,287,333 B1 | 9/2001 | Appling et al. |
| 6,290,722 B1 | 9/2001 | Wang |
| 6,312,458 B1 | 11/2001 | Golds |
| 6,315,791 B1 | 11/2001 | Gingras et al. |
| 6,315,792 B1 | 11/2001 | Armstrong et al. |
| 6,331,188 B1 | 12/2001 | Lau et al. |
| 6,331,190 B1 | 12/2001 | Shokoohi et al. |
| 6,334,868 B1 | 1/2002 | Ham |
| 6,336,937 B1 | 1/2002 | Vonesh et al. |
| 6,340,366 B2 | 1/2002 | Wijay |
| 6,344,054 B1 | 2/2002 | Parodi |
| 6,350,277 B1 | 2/2002 | Kocur |
| 6,355,055 B1 | 3/2002 | Waksman et al. |
| 6,357,104 B1 | 3/2002 | Myers |
| 6,361,637 B2 | 3/2002 | Martin et al. |
| 6,364,903 B2 | 4/2002 | Tseng et al. |
| 6,387,122 B1 | 5/2002 | Cragg |
| 6,398,803 B1 | 6/2002 | Layne et al. |
| 6,409,754 B1 | 6/2002 | Smith et al. |
| 6,419,685 B2 | 7/2002 | Di Caprio et al. |
| 6,432,133 B1 | 8/2002 | Lau et al. |
| 6,436,132 B1 | 8/2002 | Patel et al. |
| 6,451,050 B1 | 9/2002 | Rudakov et al. |
| 6,461,380 B1 | 10/2002 | Cox |
| 6,488,701 B1 | 12/2002 | Nolting et al. |
| 6,488,705 B2 | 12/2002 | Schmitt et al. |
| 6,497,722 B1 | 12/2002 | Von Oepen et al. |
| 6,500,203 B1 | 12/2002 | Thompson et al. |
| 6,503,556 B2 | 1/2003 | Harish et al. |
| 6,506,202 B1 | 1/2003 | Dutta et al. |
| 6,511,496 B1 | 1/2003 | Huter et al. |
| 6,520,986 B2 | 2/2003 | Martin et al. |
| 6,527,739 B1 | 3/2003 | Bigus et al. |
| 6,537,311 B1 | 3/2003 | Cox et al. |
| 6,540,773 B2 | 4/2003 | Dong |
| 6,540,776 B2 | 4/2003 | Sanders Millare et al. |
| 6,541,589 B1 | 4/2003 | Baillie |
| 6,551,350 B1 | 4/2003 | Thornton et al. |
| 6,551,352 B2 | 4/2003 | Clerc et al. |
| 6,554,848 B2 | 4/2003 | Boylan et al. |
| 6,558,414 B2 | 5/2003 | Layne |
| 6,558,415 B2 | 5/2003 | Thompson |
| 6,565,599 B1 | 5/2003 | Hong et al. |
| 6,585,755 B2 | 7/2003 | Jackson et al. |
| 6,589,275 B1 | 7/2003 | Ivancev et al. |
| 6,589,276 B2 | 7/2003 | Pinchasik et al. |

(56) References Cited

U.S. PATENT DOCUMENTS

| | | |
|---|---|---|
| 6,602,284 B2 | 8/2003 | Cox et al. |
| 6,605,056 B2 | 8/2003 | Eidenschink et al. |
| 6,607,551 B1 | 8/2003 | Sullivan et al. |
| 6,616,689 B1 | 9/2003 | Ainsworth et al. |
| 6,620,193 B1 | 9/2003 | Lau et al. |
| 6,626,939 B1 | 9/2003 | Burnside et al. |
| 6,629,992 B2 | 10/2003 | Bigus et al. |
| 6,645,239 B1 | 11/2003 | Park et al. |
| 6,652,574 B1 | 11/2003 | Jayaraman |
| 6,652,579 B1 | 11/2003 | Cox et al. |
| 6,669,719 B2 | 12/2003 | Wallace et al. |
| 6,673,103 B1 | 1/2004 | Golds et al. |
| 6,689,162 B1 | 2/2004 | Thompson |
| 6,709,454 B1 | 3/2004 | Cox et al. |
| 6,712,357 B1 | 3/2004 | Tranquilla |
| 6,713,357 B1 | 3/2004 | Wang et al. |
| 6,730,117 B1 | 5/2004 | Tseng et al. |
| 6,740,114 B2 | 5/2004 | Burgermeister |
| 6,770,087 B2 | 8/2004 | Layne et al. |
| 6,770,089 B1 | 8/2004 | Hong et al. |
| 6,776,771 B2 | 8/2004 | van Moorlegem et al. |
| 6,805,705 B2 | 10/2004 | Hong et al. |
| 6,849,086 B2 | 2/2005 | Cragg |
| 6,866,805 B2 | 3/2005 | Hong et al. |
| 6,872,433 B2 | 3/2005 | Seward et al. |
| 6,881,216 B2 | 4/2005 | Di Caprio et al. |
| 6,881,221 B2 | 4/2005 | Golds |
| 6,887,266 B2 | 5/2005 | Williams et al. |
| 6,893,457 B2 | 5/2005 | Dong |
| 6,923,827 B2 | 8/2005 | Campbell et al. |
| 6,945,991 B1 | 9/2005 | Brodeur et al. |
| 6,960,186 B1 | 11/2005 | Fukaya et al. |
| 7,105,018 B1 | 9/2006 | Yip et al. |
| 7,105,021 B2 | 9/2006 | Edens et al. |
| 7,108,716 B2 | 9/2006 | Burnside et al. |
| 7,112,293 B2 | 9/2006 | Dubson et al. |
| 7,115,220 B2 | 10/2006 | Dubson et al. |
| 7,118,592 B1 | 10/2006 | Dang et al. |
| 7,141,062 B1 | 11/2006 | Pinchasik et al. |
| 7,144,422 B1 | 12/2006 | Rao |
| 7,163,533 B2 | 1/2007 | Hobbs et al. |
| 7,163,553 B2 | 1/2007 | Limon |
| 7,186,263 B2 | 3/2007 | Golds et al. |
| 7,273,495 B2 | 9/2007 | Limon |
| 7,288,111 B1 | 10/2007 | Holloway et al. |
| 7,314,480 B2 | 1/2008 | Eidenschink et al. |
| 7,323,008 B2 | 1/2008 | Kantor et al. |
| 7,329,276 B2 | 2/2008 | Smith et al. |
| 7,384,411 B1 | 6/2008 | Condado |
| 7,455,687 B2 | 11/2008 | Saunders et al. |
| 7,510,571 B2 | 3/2009 | Spiridigliozzi et al. |
| 7,540,879 B2 | 6/2009 | Loaldi |
| 7,578,831 B2 | 8/2009 | Von Oepen et al. |
| 7,686,841 B2 | 3/2010 | Eidenschink et al. |
| 7,691,461 B1 | 4/2010 | Prabhu |
| 7,704,274 B2 | 4/2010 | Boyle et al. |
| 7,727,271 B2 | 6/2010 | Kujawski et al. |
| 7,967,836 B2 | 6/2011 | Warnack et al. |
| 8,066,667 B2 | 11/2011 | Hayman et al. |
| 8,221,484 B2 | 7/2012 | Wesselmann |
| 8,257,432 B2 | 9/2012 | Kaplan et al. |
| 8,444,686 B2 | 5/2013 | Holman et al. |
| 8,585,640 B2 | 11/2013 | Alpini et al. |
| 8,597,566 B2 | 12/2013 | Eskaros et al. |
| 8,672,990 B2 | 3/2014 | Holman et al. |
| 8,858,863 B2 | 10/2014 | Venturelli |
| 8,926,688 B2 | 1/2015 | Burkart et al. |
| 8,979,886 B2 | 3/2015 | Campbell et al. |
| 9,149,612 B2 | 10/2015 | Chuter |
| 9,370,643 B2 | 6/2016 | Hedberg et al. |
| 9,370,647 B2 | 6/2016 | Campbell et al. |
| 9,622,888 B2 | 4/2017 | Armstrong et al. |
| 9,669,194 B2 | 6/2017 | Campbell et al. |
| 9,682,219 B2 | 6/2017 | Venturelli |
| 9,770,352 B2 | 9/2017 | Kanjickal et al. |
| 9,901,715 B2 | 2/2018 | Cully et al. |
| 2001/0020181 A1 | 9/2001 | Layne |
| 2001/0025130 A1 | 9/2001 | Tomonto |
| 2002/0007102 A1 | 1/2002 | Salmon et al. |
| 2002/0049408 A1 | 4/2002 | Van Moorlegem et al. |
| 2002/0111668 A1 | 8/2002 | Smith |
| 2002/0151964 A1 | 10/2002 | Smith et al. |
| 2002/0165601 A1 | 11/2002 | Clerc |
| 2003/0060756 A1 | 3/2003 | Hayman et al. |
| 2003/0208260 A1 | 11/2003 | Lau et al. |
| 2003/0236563 A1 | 12/2003 | Fifer |
| 2004/0019373 A1 | 1/2004 | Casey et al. |
| 2004/0024442 A1 | 2/2004 | Sowinski et al. |
| 2004/0024448 A1 | 2/2004 | Chang et al. |
| 2004/0030377 A1 | 2/2004 | Dubson et al. |
| 2004/0033364 A1 | 2/2004 | Spiridigliozzi et al. |
| 2004/0096532 A1 | 5/2004 | Dubson et al. |
| 2004/0096533 A1 | 5/2004 | Dubson et al. |
| 2004/0167635 A1 | 8/2004 | Yachia et al. |
| 2004/0172127 A1 | 9/2004 | Kantor |
| 2004/0236402 A1 | 11/2004 | Layne et al. |
| 2005/0010281 A1 | 1/2005 | Yodfat et al. |
| 2005/0125071 A1 | 6/2005 | Nahleili |
| 2005/0137675 A1 | 6/2005 | Dubson et al. |
| 2005/0154449 A1 | 7/2005 | Elmaleh |
| 2005/0182474 A1 | 8/2005 | Jones et al. |
| 2005/0186243 A1 | 8/2005 | Hunter et al. |
| 2005/0209672 A1 | 9/2005 | George et al. |
| 2005/0228480 A1 | 10/2005 | Douglas et al. |
| 2006/0009835 A1 | 1/2006 | Osborne et al. |
| 2006/0036308 A1 | 2/2006 | Goshgarian |
| 2006/0036311 A1 | 2/2006 | Nakayama et al. |
| 2006/0085065 A1 | 4/2006 | Krause et al. |
| 2006/0122691 A1 | 6/2006 | Richter |
| 2006/0184237 A1 | 8/2006 | Weber et al. |
| 2006/0190072 A1 | 8/2006 | Das |
| 2006/0259133 A1 | 11/2006 | Sowinski et al. |
| 2006/0266474 A1 | 11/2006 | Burnside et al. |
| 2006/0271157 A1 | 11/2006 | Edens et al. |
| 2006/0271165 A1 | 11/2006 | Yip et al. |
| 2006/0287709 A1 | 12/2006 | Rao |
| 2006/0293743 A1 | 12/2006 | Andersen et al. |
| 2007/0055365 A1 | 3/2007 | Greenberg et al. |
| 2007/0073383 A1 | 3/2007 | Yip et al. |
| 2007/0129791 A1 | 6/2007 | Balaji |
| 2007/0208412 A1 | 9/2007 | Elmaleh |
| 2007/0250146 A1 | 10/2007 | Cully et al. |
| 2008/0319388 A1 | 12/2008 | Slattery et al. |
| 2009/0054967 A1 | 2/2009 | Das |
| 2009/0069878 A1 | 3/2009 | Weber et al. |
| 2009/0138070 A1 | 5/2009 | Holzer et al. |
| 2009/0182413 A1 | 7/2009 | Burkart et al. |
| 2010/0069839 A1 | 3/2010 | Holman et al. |
| 2010/0222870 A1 | 9/2010 | Kaplan et al. |
| 2011/0087191 A1 | 4/2011 | Scheuermann |
| 2012/0071912 A1 | 3/2012 | Campbell et al. |
| 2012/0109283 A1 | 5/2012 | Burkart et al. |
| 2012/0253380 A1 | 10/2012 | Venturelli |
| 2012/0330232 A1 | 12/2012 | Hedberg et al. |
| 2013/0018406 A1 | 1/2013 | Campbell et al. |
| 2013/0253466 A1 | 9/2013 | Campbell et al. |
| 2014/0066896 A1 | 3/2014 | Tilson et al. |
| 2014/0066897 A1 | 3/2014 | Campbell et al. |
| 2014/0066898 A1 | 3/2014 | Cully et al. |
| 2014/0135891 A1 | 5/2014 | Poehlmann et al. |
| 2014/0172066 A1 | 6/2014 | Goepfrich et al. |
| 2014/0276406 A1 | 9/2014 | Campbell et al. |
| 2014/0277346 A1 | 9/2014 | Kanjickal et al. |
| 2014/0277374 A1 | 9/2014 | Kovach |
| 2014/0378896 A1 | 12/2014 | Venturelli |
| 2015/0133988 A1 | 5/2015 | Chuter |
| 2016/0143759 A1 | 5/2016 | Bohn et al. |
| 2016/0243340 A1 | 6/2016 | Campbell et al. |
| 2017/0172776 A1 | 6/2017 | Kanjickal et al. |
| 2017/0340464 A1 | 11/2017 | Kovach et al. |
| 2017/0340465 A1 | 11/2017 | Kanjickal et al. |
| 2018/0049898 A1 | 2/2018 | Armstrong et al. |

(56) References Cited

U.S. PATENT DOCUMENTS

FOREIGN PATENT DOCUMENTS

| | | | |
|---|---|---|---|
| EP | 0951877 | A2 | 10/1999 |
| EP | 1110561 | A2 | 6/2001 |
| EP | 1927327 | B1 | 6/2008 |
| JP | 2005535414 | A | 11/2005 |
| JP | 2014520632 | A | 8/2014 |
| WO | 1995017223 | A1 | 6/1995 |
| WO | WO9526695 | A2 | 10/1995 |
| WO | WO9621404 | A1 | 7/1996 |
| WO | 1999034855 | A1 | 7/1999 |
| WO | WO9934855 | A1 | 7/1999 |
| WO | 2000043051 | A1 | 7/2000 |
| WO | WO0042949 | A2 | 7/2000 |
| WO | 2000049971 | A1 | 8/2000 |
| WO | WO0045741 | A1 | 8/2000 |
| WO | WO0121101 | A1 | 3/2001 |
| WO | 2002022024 | A2 | 3/2002 |
| WO | 2003007795 | A3 | 1/2003 |
| WO | WO03057075 | A2 | 7/2003 |
| WO | WO03057077 | A1 | 7/2003 |
| WO | 2004016199 | A1 | 2/2004 |
| WO | 2004093941 | A2 | 11/2004 |
| WO | 2005096997 | A2 | 10/2005 |
| WO | 2006029617 | A1 | 3/2006 |
| WO | 2006081568 | A1 | 8/2006 |
| WO | 2006124824 | A1 | 11/2006 |
| WO | 2009066330 | A1 | 5/2009 |
| WO | 2010037141 | A1 | 4/2010 |
| WO | 2013009740 | A1 | 1/2013 |
| WO | 2013040522 | A2 | 3/2013 |
| WO | 2013096854 | A3 | 6/2013 |
| WO | 2014152684 | A2 | 9/2014 |
| WO | 2014158516 | A1 | 10/2014 |
| WO | 2015073114 | A1 | 5/2015 |
| WO | 2016086202 | A2 | 6/2016 |

OTHER PUBLICATIONS

International Search Report and Written Opinion issued in PCT/US2009/000144, dated Jun. 5, 2009, 14 pages.
International Search Report and Written Opinion issued in PCT/US2015/062799, dated Jul. 27, 2016, 17 pages.
International Search Report and Written Opinion issued in PCT/US2016/039565, dated Oct. 10, 2016, 20 pages.
International Search Report issued in PCT/US0001715, dated Oct. 27, 2000, 7 pages.
Nakayama, Y. et al., "Fabrication of micropored elastomeric film-covered stents and acute-phase performances," Development of Covered Stents, 2002; 52-61.
Nishi, S. et al., "Newly Developed Stent Graft with Micropored and Heparin Impregnated SPU Film, Long-Term Follow-up Study in Vivo", Interventional Neuroradiology, 7 (Suppl 1): 161-166, 2001.
Wilson, Eric et al., "Deployment and Healing of an ePTFE Encapsulated Stent Endograft in the Canine Aorta," Annals of Vascular Surgery, (1997), vol. 11, No. 4, pp. 354-358.
International Preliminary Report on Patentability issued in PCT/US2015/062799, dated Jun. 8, 2017, 10 pages.

BALLOON EXPANDABLE ENDOPROSTHESIS

CROSS-REFERENCE TO RELATED APPLICATION

This application is a national phase application of PCT Application No. PCT/US2015/062799, internationally filed on Nov. 25, 2015, which is a continuation of U.S. application Ser. No. 14/950,165, filed Nov. 24, 2015, which claims the benefit of U.S. Provisional Application No. 62/085,066, filed Nov. 26, 2014, all of which are herein incorporated by reference in their entireties.

FIELD

The present disclosure generally relates to endoprostheses for treating vasculature, and more particularly, to balloon expandable endoprotheses.

BACKGROUND

Endoprostheses are valuable tools for improving and saving lives. In many instances, an endoprosthesis is inserted into a vasculature in an "undeployed" state and must be expanded into a "deployed" state. To transition the endoprosthesis between these two states, a balloon may be located within the endoprosthesis in its undeployed state and inflated, with the expansion of the balloon pushing the endoprosthesis into its deployed state. However, in many instances the balloon extends beyond the longitudinal length of the endoprosthesis. As a result, those portions of the balloon unconstrained by the endoprosthesis expand rapidly in comparison to those portions of the balloon within the endoprosthesis, causing the balloon to exert a longitudinal force on the endoprosthesis that causes the endoprosthesis to diminish in longitudinal length. Aspects of the present disclosure reduce that effect in order to create an improved endoprosthesis, among other features and benefits discussed below in more detail.

SUMMARY OF THE DISCLOSURE

In one embodiment, a medical device, comprises a stent-graft defining a first free end, a second free end, and an intermediate portion between the first and second free ends, the stent-graft having an undeployed state with an undeployed diameter and an undeployed longitudinal length between the first free end and the second free end and a deployed state with a deployed diameter and a deployed longitudinal length between the first free end and the second free end. The stent-graft includes a stent portion and a graft portion. The medical device further comprises a catheter assembly onto which the stent-graft is assembled in the undeployed state. The catheter assembly includes a balloon and a cover concentrically surrounding the balloon. The intermediate portion of the stent-graft imparts a resistance to expansion of the balloon at the intermediate portion of the stent-graft and the cover also imparts a resistance to expansion of the balloon to reduce a difference in an expansion rate of the balloon at the free ends of the stent-graft relative to an expansion rate of the balloon at the intermediate portion of the stent-graft so as to reduce longitudinal compression of the stent-graft as the balloon expands the stent-graft from its undeployed state to its deployed state.

In one variation, the deployed length of the stent-graft is at least 85% of the undeployed length of the stent-graft.

In one variation, the cover includes reinforcing portions configured to resist inflation of corresponding shoulder portions of the balloon so as to reduce longitudinal compression of the stent-graft as the balloon expands the stent-graft from its undeployed state to its deployed state.

In one variation, the stent portion of the stent graft includes a plurality of ring stent elements that are separate components connected by the graft portion of the stent-graft.

In one variation, the graft portion is configured to store longitudinal length of the stent-graft when the stent-graft is in the undeployed state.

In one variation, the graft portion of the stent-graft is formed of ePTFE.

In another embodiment, a medical device comprises a stent-graft defining a first free end, a second free end, and an intermediate portion between the first and second free ends, the stent-graft having an undeployed state with undeployed longitudinal length between the first free end and the second free end and a deployed state with a deployed longitudinal length between the first free end and the second free end. The stent-graft includes a stent portion, and a graft portion. The catheter assembly, onto which the stent-graft is assembled in the undeployed state, includes a balloon and a cover concentrically surrounding the balloon, the intermediate portion of the stent-graft imparting a resistance to expansion of the balloon at the intermediate portion of the stent-graft and the cover also imparting a resistance to expansion of the balloon such that the deployed length of the stent-graft is at least 85% of the undeployed length of the stent-graft.

In one variation, the graft portion of the stent-graft is formed of ePTFE.

In one embodiment, a medical device comprises a stent-graft including: an inner ePTFE graft element, an outer ePTFE graft element, and a multiplicity of ringed stent elements positioned between the inner ePTFE graft element and the outer ePTFE graft element, the stent-graft having an undeployed state with a undeployed diameter and a deployed state with a deployed diameter greater than the undeployed diameter; and a catheter assembly including a balloon concentrically surrounded by a cover, the cover including reinforcing portions configured to resist inflation of corresponding shoulder portions of the balloon so as to reduce longitudinal compression of the stent-graft as the balloon expands the stent-graft from its undeployed state to its deployed state.

In one variation, the reinforcing portions of the cover maintain an expansion profile of the balloon that diminishes an amount of radial expansion of the shoulder portions of the balloon relative to a middle portion of the balloon as the balloon is inflated.

In one variation, the multiplicity of ringed stent elements are configured to store longitudinal length when the stent-graft is in the undeployed state.

In one variation, the stent-graft has an undeployed length in the undeployed state and a deployed length in the deployed state, wherein the deployed length is between 85% and 99% of the undeployed length.

In one variation, the deployed diameter is about 10 mm, and wherein the stent-graft is sufficiently flexible to withstand a bend radius of less than about 8 mm without kinking when in the deployed state.

In one variation, the deployed diameter is about 10 mm, and wherein the stent-graft has a radial strength of between about 11 psi and about 12 psi when in the deployed state.

In one variation, at least one ringed stent element is spaced apart between about 0.5 mm and about 2.0 mm from an adjacent ringed stent element when the stent-graft is in the deployed state.

In one variation, the at least one ringed stent element is spaced apart between about 0.0 mm and about 0.2 mm from the adjacent ringed stent element when the stent-graft is in the undeployed state.

In one variation, the multiplicity of ringed stent elements comprise interconnected wire frames.

In one variation, an internal angle of one of the interconnected wire frames is about 90 degrees when the stent-graft is in the deployed state.

In one variation, the multiplicity of ringed stent elements comprise a single row of interconnected diamond shaped wire frames.

In one variation, the multiplicity of ringed stent elements comprise stainless steel.

In one variation, an apex of a first ringed stent element is out of phase with an adjacent apex of a second ringed stent element along a longitudinal axis.

In another embodiment, a medical device comprises a stent-graft having an undeployed state with an undeployed diameter and an undeployed length, and a deployed state with a deployed diameter and a deployed length, the stent-graft including: an inner graft element; an outer graft element; and a plurality of ringed stent elements positioned between and attached to the inner graft element and the outer graft element; and a catheter assembly including: a balloon having a cone-shaped end; a cover concentrically surrounding the balloon, the cover having a middle portion and a reinforcing portion concentrically surrounding the cone-shaped end of the balloon, the reinforcing portion of the cover having a higher density than a density of the middle portion of the cover in order to maintain an expansion profile that reduces longitudinal compression of the graft-stent.

In one variation, a spacing of at least some of the plurality of ringed stent elements when the stent-graft is in its undeployed state stores longitudinal length that is recovered by the stent-graft in its deployed state.

In one variation, the deployed length exhibits less than 1% foreshortening compared to the undeployed length.

In one variation, the stent-graft is compacted onto the cover so as to resist movement of the stent-graft relative to the balloon prior to deployment.

In one variation, the reinforcing portion of the cover has a radial strength that is greater than a radial strength of the middle portion.

In one variation, the outer graft element includes an outer surface comprising ePTFE in contact with an inner surface of the cover, and wherein the inner surface of the cover comprises ePTFE.

In one variation, the balloon comprises nylon.

In one variation, a luminal surface of the inner graft element comprises an antithrombogenic coating.

In one variation, the reinforcing portion of the cover restricts expansion of the cone-shaped end of the balloon during inflation of the balloon.

In one variation, the reinforcing portion of the cover includes an axially compressed portion of the cover.

In one variation, the reinforcing portion of the cover includes a pleated portion of the cover.

In one variation, pleatings in the pleated portion of the cover correspond to pleatings in a pleated portion of the balloon.

In another embodiment, a method of making an stent-graft comprises: placing a plurality of ringed stent elements along a longitudinal axis and between an inner graft element and outer graft element; compressing the plurality of ringed stent elements, the inner graft element, and the outer graft element into a compressed configuration; and moving at least two of the plurality of ringed stent elements closer together to store longitudinal length so that when the stent-graft expands into a deployed configuration, the stored longitudinal length is recovered.

In another embodiment, a method of making a deployment system comprises assembling a stent graft to a deployment device, the stent-graft having a first free end, a second free end, an intermediate portion between the first and second free ends, and a first diameter in an undeployed state and the deployment device having a balloon and a cover surrounding the balloon, the stent-graft assembled to the deployment device such that the stent-graft surrounds the cover and the balloon, the intermediate portion of the stent-graft imparting a resistance to expansion of the balloon and the cover also imparting a resistance to expansion of the balloon to reduce a difference in an expansion rate of the balloon at the intermediate portion of the stent-graft relative to an expansion rate of the balloon at the first and second free ends of the stent-graft so as to reduce longitudinal compression of the stent-graft upon expansion of the balloon to transition the stent-graft from the undeployed state to the deployed state.

In one variation, moving the at least two of the plurality of ringed stent elements closer together comprises moving the at least two of the plurality of ringed stent elements from a separation distance of between about 0.5 mm and about 2.0 mm to a separation distance of between about 0.0 mm and about 0.2 mm.

In one variation, the method further includes placing a cover over a balloon, the cover having at least one reinforcing portion overlaying a shoulder of the balloon, the at least one reinforcing portion providing increased resistance to inflation relative to a middle portion of the cover; and placing the stent-graft over the middle portion of the cover, such that the reinforcing portion of the cover reduces longitudinal compressing forces exerted on the stent-graft during inflation of the balloon.

In one variation, the stent-graft exhibits greater than 99% longitudinal efficiency when the stent-graft expands from the compressed configuration into a deployed configuration.

In another embodiment, a method for treating a patient includes: inserting a stent-graft into a vessel of the patient, the stent-graft having a first length and a first diameter, the stent-graft surrounding a middle portion of a cover that concentrically surrounds a balloon, the cover and the balloon each having a length that is greater than the first length of the stent-graft such that at least one shoulder of the balloon and a corresponding portion of the cover are outside of the stent-graft, the corresponding portion of the cover being reinforced to provide greater resistance to inflation of the shoulder of the balloon than a middle portion of the cover provides to a middle portion of the balloon; and applying a pressure to the balloon to expand the stent-graft to a second diameter that is greater than the first diameter and to expand the stent-graft to a second length, the reinforced portion of the cover restricting inflation of the shoulder of the balloon to limit longitudinal compressing forces on the stent-graft.

In one variation, the second length of the stent-graft is at least 85% of the first length of the stent-graft.

In one variation, the reinforcing portion of the cover includes scrunched portions of the cover.

In one variation, the reinforcing portion of the cover includes pleated portions of the cover.

In one variation, pleatings in the pleated portions of the cover correspond to pleatings in pleated portions of the balloon.

In another embodiment, a method for treating a patient includes: inserting a stent-graft into a vessel of the patient, the stent-graft having a first length and a first diameter, the stent-graft surrounding a cover that surrounds a balloon, the stent-graft including a plurality of stent elements that are positioned to store longitudinal length; and applying a pressure to the balloon to expand the stent-graft to a second diameter that is greater than the first diameter and a second length, wherein expanding the stent-graft recovers the stored longitudinal length.

In one variation, the second length of the stent-graft is between 85% and 99% of the first length of the stent-graft.

In one variation, the second length of the stent-graft is at least 85% of the first length of the stent-graft.

In one variation, the second length of the stent-graft is at least 99% of the first length of the stent-graft.

In another embodiment, a method for treating a patient includes: inserting a stent-graft into a vessel of the patient, the stent-graft having a first free end, a second free end, an intermediate portion between the first and second free ends, and a first diameter, the stent-graft surrounding a cover that surrounds a balloon, the stent-graft including a plurality of stent elements; and applying a pressure to the balloon to expand the stent-graft from an undeployed state to a deployed state having a second diameter that is greater than the first diameter, the intermediate portion of the stent-graft resisting expansion of the balloon and the cover also resisting expansion of the balloon to reduce a difference in an expansion rate of the balloon at the intermediate portion of the stent-graft relative to an expansion rate of the balloon at the first and second free ends of the stent-graft so as to reduce longitudinal compression of the stent-graft as the balloon expands the stent-graft from the undeployed state to the deployed state.

In one variation, the second length of the stent-graft is between 85% and 99% of the first length of the stent-graft.

In one variation, the stent-graft defines a first length in the undeployed state and a second length in the deployed state that is at least 85% of first length.

In one variation, the stent-graft defines a first length in the undeployed state and a second length in the deployed state that is at least 99% of first length.

BRIEF DESCRIPTION OF THE DRAWINGS

The features and advantages of the present disclosure will become more apparent from the detailed description set forth below when taken in conjunction with the drawings, wherein.

DETAILED DESCRIPTION OF THE ILLUSTRATED EMBODIMENTS

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

The terms "endoprosthetic device," "endoprosthesis," "vascular device," and the like can refer, throughout the specification and in the claims, to any medical device capable of being implanted and/or deployed within a body lumen. In various embodiments, an endoprosthesis can comprise a stent, a stent-graft, a graft, a filter, an occluder, a balloon, a lead, and energy transmission device, a deployable patch, an indwelling catheter, and the like.

In addition, throughout this specification and claims, the delivery systems described herein can, in general, include an endoprosthesis constrained by a "covering member" or "sheath." The covering member or sheath can, in various embodiments, comprise a sheet of material that is fitted about an endoprosthesis. As used throughout the specification and in the claims, the term "elongate member" can refer to a shaft-like structure such as a catheter, guidewire, introducer sheath, or the like. In various embodiments, an endoprosthesis can be mounted or loaded on a catheter, also referred to herein as an inner shaft, and, in a constrained diameter, fit within an introducer sheath, also referred to herein as an outer shaft.

Further, the term "distal" refers to a relative location that is farther from a location in the body at which the medical device was introduced. Similarly, the term "distally" refers to a direction away from a location in the body at which the medical device was introduced.

The term "proximal" refers to a relative location that is closer to the location in the body at which the medical device was introduced. Similarly, the term "proximally" refers to a direction towards a location in the body at which the medical device was introduced.

With continuing regard to the terms proximal and distal, this disclosure should not be narrowly construed with respect to these terms. Rather, the devices and methods described herein may be altered and/or adjusted relative to the anatomy of a patient.

As used herein, the term "constrain" may mean (i) to limit expansion, occurring either through self-expansion or expansion assisted by a device, of the diameter of an expandable implant, or (ii) to cover or surround, but not otherwise restrain, an expandable implant (e.g., for storage or biocompatibility reasons and/or to provide protection to the expandable implant and/or the vasculature).

As used herein, the term "vessel" refers to any luminal or tubular structure within the body to which these constructs can be utilized. This includes, but is not limited to, vascular blood vessels, vascular defects such as arteriovenous malformations, aneurysm, or others, vessels of the lymphatic system, esophagus, intestinal anatomy, sinuous cavity, urogenital system, or other such systems or anatomical features. Embodiments of the present invention are also suitable for the treatment of a malignant disease (e.g., cancer) within or associated with a vessel.

Figure 1A:
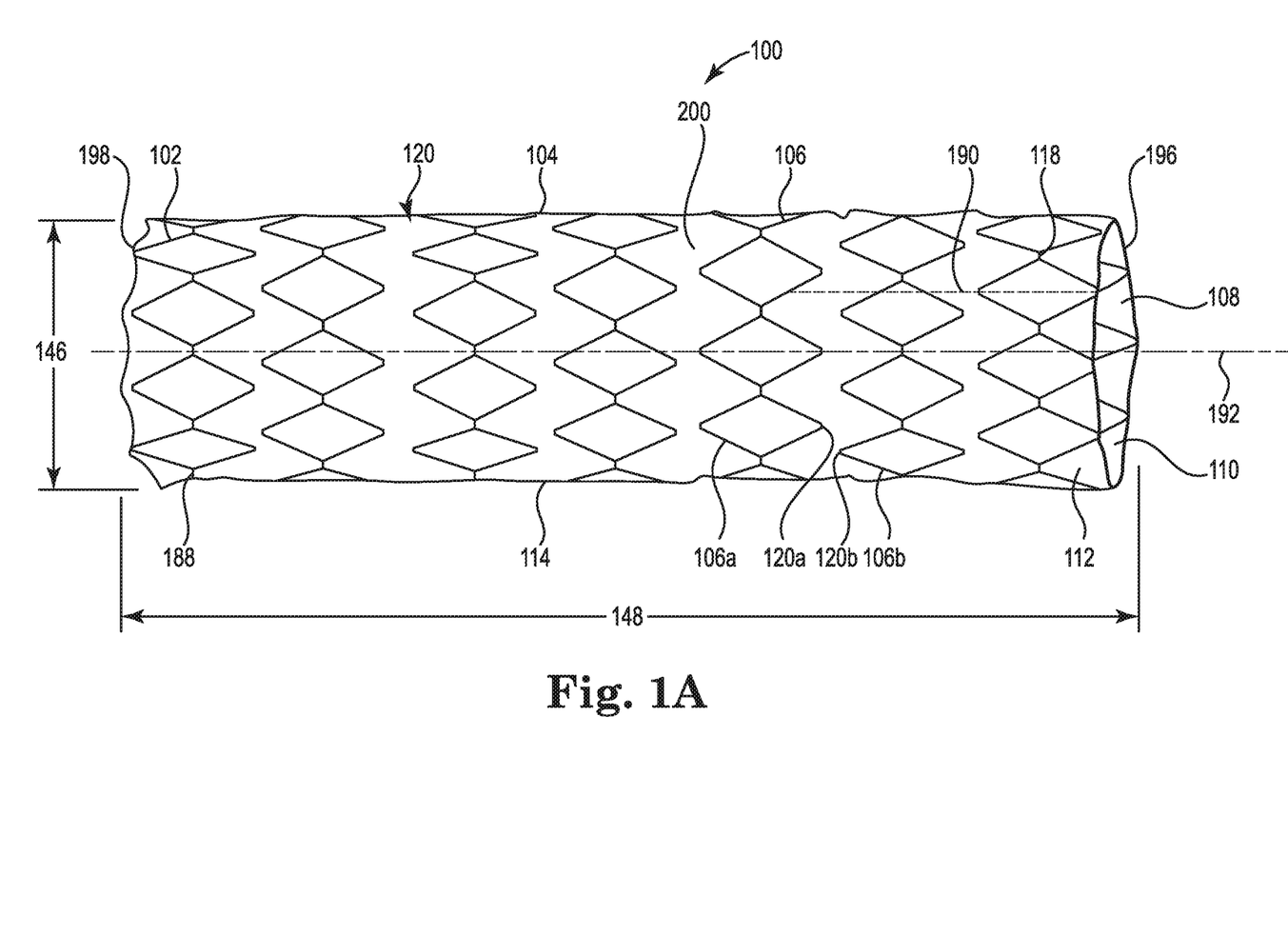
FIGS. 1A and 1B illustrate side views of an endoprosthesis in accordance with embodiments of the present disclosure.
Figure 1B:
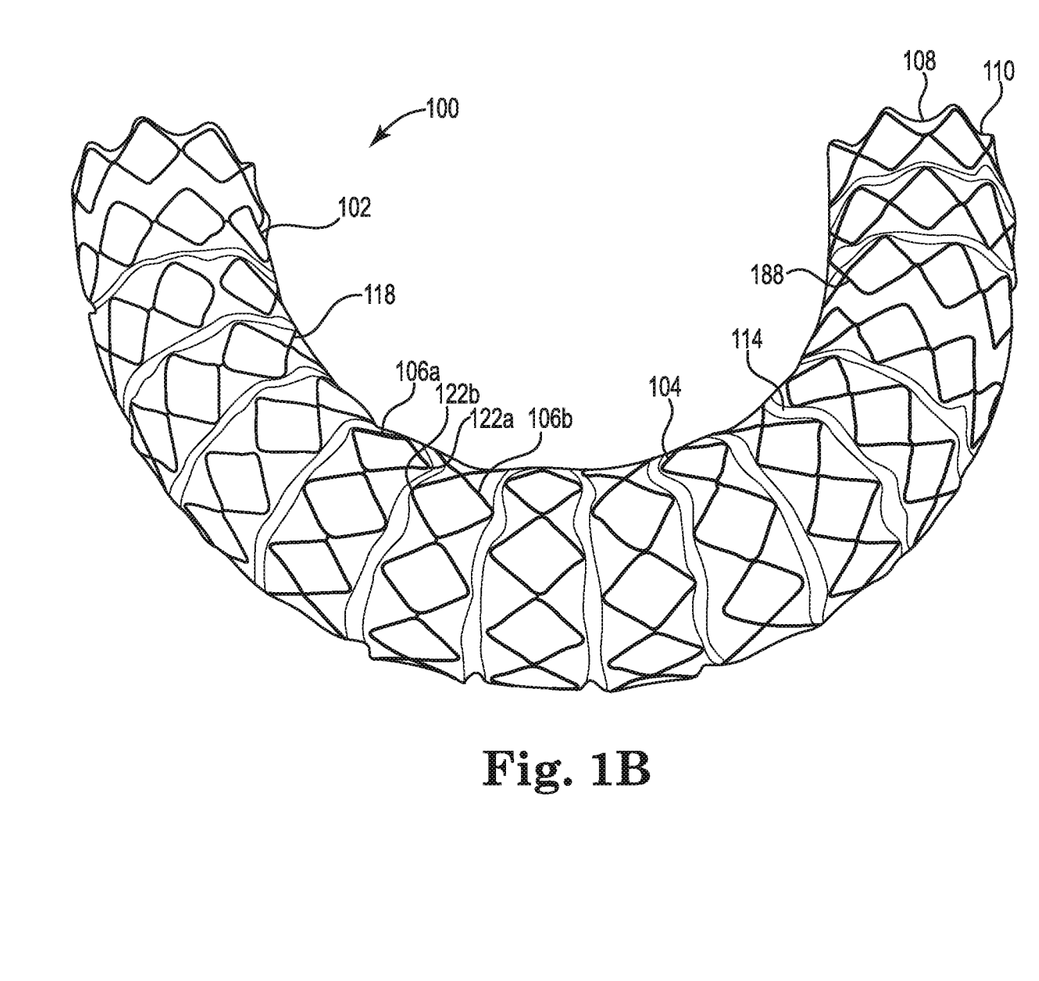

With initial reference to FIGS. 1A and 1B, an endoprosthesis 100 is illustrated. Endoprosthesis 100 may comprise, for example, an expandable stent-graft. In various embodiments, endoprosthesis 100 comprises a balloon expandable stent-graft. Although endoprosthesis 100 will be herein described as a balloon expandable stent-graft, endoprosthesis 100 may comprise other implantable, expandable medical devices, including a self-expandable stent-graft.

In various embodiments, stent-graft 100 comprises a stent member 102. For example, stent member 102 can comprise one or more ringed stent elements 104. As will be discussed in greater detail, ringed stent elements 104 can be positioned adjacent to one another along a longitudinal axis 192 of stent-graft 100. In various embodiments, ringed stent elements 104 are evenly spaced from each other (i.e., uniformly distributed along the longitudinal axis). In other embodiments, one or more ringed stent elements 104 can be spaced apart from one another at different spacing along longitudinal axis 192 (i.e., non-uniformly distributed along the longitudinal axis). Any arrangement of ringed stent elements 104 is within the scope of the present disclosure.

Ringed stent elements 104 can comprise, for example, interconnected wire frames 106 arranged in a circular pattern. For example, ringed stent elements 104 can comprise a single row of interconnected wire frames 106. One or more points 118 of a wire frame 106 can be in contact with and connected to points 118 of adjacent wire frames 106. In various embodiments, ringed stent elements 104 can comprise a multiplicity of individual wire frames 106 formed independently of one another and connected to each other at one or more points 118. In other embodiments, wire frames 106 are formed together as a single interconnected stent element 104.

In various embodiments, ringed stent elements 104 can vary from each other in stiffness. For example, one or more ringed stent elements 104 having an increased stiffness can be located at a distal and/or proximal end of stent-graft 100. Further, one or more ringed stent elements 104 having reduced stiffness can be located away from a distal and/or proximal end of stent-graft 100. Any combination of ringed stent elements 104, including multiple elements comprising different stiffness from each other, is within the scope of the present disclosure.

Wire frames 106 can comprise a polygon, such as, for example, a parallelogram. In various embodiments, wire frames 106 comprise a diamond shape. In other embodiments, wire frames 106 can comprise a square or rectangular shape. Any shape of wire frames 106, including shapes that are not polygonal (such as ovoid or rounded shapes) or shapes that include undulations or bends, are within the scope of the present disclosure.

In various embodiments, wire frames 106 comprise a metal material. For example, wire frames 106 can comprise a steel, such as stainless steel or other alloy. In other embodiments, wire frames 106 can comprise a shape memory alloy, such as, for example, Nitinol. In yet other embodiments, wire frames 106 comprise a non-metallic material, such as a polymeric material. Further, the material of wire frames 106 can be permanent (i.e., non-bioabsorbable) or bioabsorbable. Any material of wire frames 106 having sufficient strength is within the scope of the present disclosure.

For example, ringed stent elements 104 can, for example, be cut from a single metallic tube. In various embodiments, ringed stent elements 104 are laser cut from a stainless steel tube. However, any manner of forming ringed stent elements 104 and/or wire frames 106 is within the scope of the present disclosure.

Endoprosthesis 100 can further comprise a graft member 114. Graft member 114 may, for example, provide a lumen through which blood may flow from one end to another. Further, as will be discussed in greater detail, graft member 114 can comprise a number of layers or elements secured together to form a single graft member 114.

Graft member 114 can comprise, for example, an inner graft element 108. In various embodiments, stent member 102 is positioned concentrically around inner graft element 108. For example, inner graft element 108 can comprise a layer of polymeric material having a luminal surface 110 that is in contact with blood flow within a vessel. Stent member 102 can surround, be in contact with, and provide support to inner graft element 108.

In various embodiments, inner graft element 108 comprises a polymeric membrane capable of providing a bypass route to avoid vessel damage or abnormalities, such as aneurysms. Inner graft element 108 can comprise, for example, expanded polytetrafluoroethylene (ePTFE), polyester, polyurethane, fluoropolymers, such as perfluoroelastomers and the like, polytetrafluoroethylene, silicones, urethanes, ultra-high molecular weight polyethylene, aramid fibers, and combinations thereof. Other embodiments for a graft member material can include high strength polymer fibers such as ultra-high molecular weight polyethylene fibers (e.g., Spectra®, Dyneema Purity®, etc.) or aramid fibers (e.g., Technora®, etc.). Any graft member that is capable of providing a lumen for fluid flow within the body of a patient is within the scope of the present disclosure.

Inner graft element 108 can comprise, for example, one or more layers of a polymeric material. In various embodiments, inner graft element 108 comprises a polymeric material continuously wrapped over a substrate or mandrel to form a generally tubular member. For example, inner graft element 108 can be constructed with circumferential-, helical-, or axial-orientations of the polymeric material. "Orientations," as used herein, generally refers to a directional property of a component or material (e.g., the polymetric material) often with reference to the longitudinal axis 192. Orientations may also be used to refer to directional properties of certain features, such as, for example, orientations of the strength of the material.

In the embodiments discussed above, the polymeric material can be wrapped generally perpendicular to the longitudinal axis of the mandrel or substrate, i.e., circumferentially wrapped. In other embodiments, the material can be wrapped at an angle between greater than 0 degrees and less than 90 degrees relative to the longitudinal axis of the mandrel or substrate, i.e., helically wrapped. In yet other embodiments, the polymeric material can be wrapped generally parallel to the longitudinal axis of the mandrel or substrate, i.e., axially (or longitudinally) wrapped.

In various embodiments, inner graft element 108 may comprise a coating on luminal surface 110. For example, a therapeutic agent such as antithrombogenic coating may be applied to luminal surface 110. In various embodiments, a heparin coating is applied to luminal surface 110.

Graft member 114 can further comprise, for example, an outer graft element 112. In various embodiments, outer graft element 112 concentrically surrounds at least a portion of stent member 102. For example, outer graft element 112 can concentrically surround stent member 102 and inner graft element 108, essentially sandwiching ringed stent elements 104 of stent member 102 between the two graft elements 108 and 112.

Similarly to inner graft element 108, outer graft element 112 can comprise, for example, expanded polytetrafluoroethylene (ePTFE), polyester, polyurethane, fluoropolymers, such as perfluoroelastomers and the like, polytetrafluoroethylene, silicones, urethanes, ultra-high molecular weight polyethylene, aramid fibers, and combinations thereof. Outer graft element 112 can include high strength polymer fibers such as ultra-high molecular weight polyethylene fibers (e.g., Spectra®, Dyneema Purity®, etc.) or aramid fibers (e.g., Technora®, etc.). Further, outer graft element 112 can comprise one or more layers of polymeric material, and may be a tube or a wrapped element as described in connection with inner graft element 108. In various embodiments, inner graft element 108 and outer graft element 112 comprise the same polymeric material. In other embodiments, inner graft element 108 and outer graft element 112 comprise different polymeric materials.

In such embodiments, inner graft element 108 and outer graft element 112 can orient and maintain the position of each of a multiplicity of ringed stent element 104. For example, each ringed stent element 104 of stent member 102 can be positioned at a desired location along inner graft element 108 and then surrounded by outer graft element 112. In various embodiments, after ringed stent elements 104 are properly positioned along inner graft element 108, inner graft element 108 and outer graft element 112 are bonded together. For example, heat can be applied to bond inner graft element 108 and outer graft element 112 together, thereby maintaining the position of ringed stent elements 104 with respect to graft member 114.

In various embodiments, ringed stent elements 104 are spaced apart at a desired distance from each other. For example, each of ringed stent element 104 can be positioned at between about 0 mm (i.e., one ringed stent element 104 abutting another) and about 4 mm apart from each other. In various embodiments, each of ringed stent element 104 can be between about 1.0 mm and about 2.0 mm apart from each other, and in particular embodiments are between about 1.1 mm and 1.5 mm from each other. Although described with reference to specific embodiments, ringed stent elements 104 of stent member 102 can be spaced any distance apart, including multiple different spacings within the same stent member 102.

Further, in embodiments in which stent member 102 comprises spaced apart ringed stent element 104, stent-graft 100 can comprise one or more intra-ring graft segments 120. For example, intra-ring graft segments 120 can comprise the portion of inner graft element 108 and outer graft element 112 located between adjacent ringed stent element 104. As will be discussed further, the properties of intra-ring graft segments 120, including the length of segments 120, can be manipulated to provide desired properties to stent-graft 100.

In various embodiments, a first ringed stent element 106a comprises a first apex 120a and a second ringed stent element 106b comprises a second apex 120b. First apex 120a and second apex 120b can be adjacent to each other. For example, first ringed stent element 106a and second ringed stent element 106b can be oriented with respect to each other such that first apex 120a and second apex 120b are in a common plane 190 orthogonal to a longitudinal axis 192. Stated another way, first apex 120a and second apex 120b are in phase with each other. In other embodiments, first apex 120a and second apex 120b are not in a common plane orthogonal to longitudinal axis 192 (i.e., apices 120a and 120b are out of phase, or are otherwise not coplanar with each other). Although described with reference to specific embodiments, any orientation of ringed stent elements 104, including multiple different orientations with the same medical device (i.e., stent-graft) is within the scope of the present disclosure.

Stent-graft 100 can be delivered to and deployed within a treatment area of a patient. For example, with initial reference to FIGS. 2A and 2B, stent-graft 100 can be prepared and mounted to a catheter assembly 260 comprising a catheter tube 262 with a continuous lumen 264. A cover 266 can coaxially surround a balloon 268, which is coupled to catheter tube 262 and continuous lumen 264 at or near the distal end of catheter tube 262. Attachment of cover 266 to catheter tube 262 can be accomplished in various ways, including adhering the proximal and distal ends of cover 266 to catheter tube 262 using an adhesive, such as, for example, a cyanoacrylate adhesive. Further, polymeric tape and/or film may be used to secure the proximal and distal ends of cover 266 to catheter tube 262.

Figure 2A:
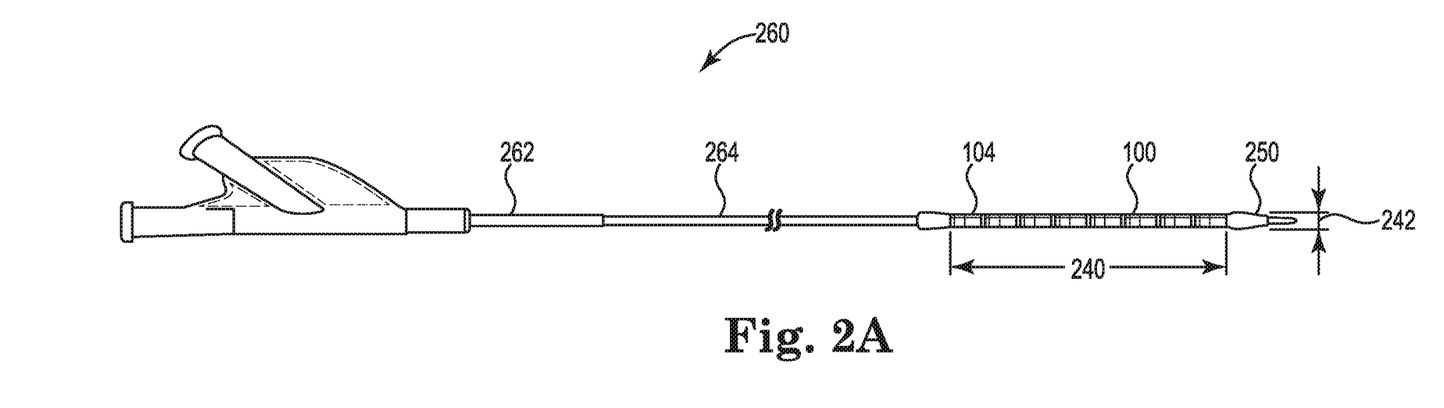
FIGS. 2A and 2B illustrate a side view and a partial cross section of an endoprosthesis delivery system in accordance with embodiments of the present disclosure.
Figure 2B:
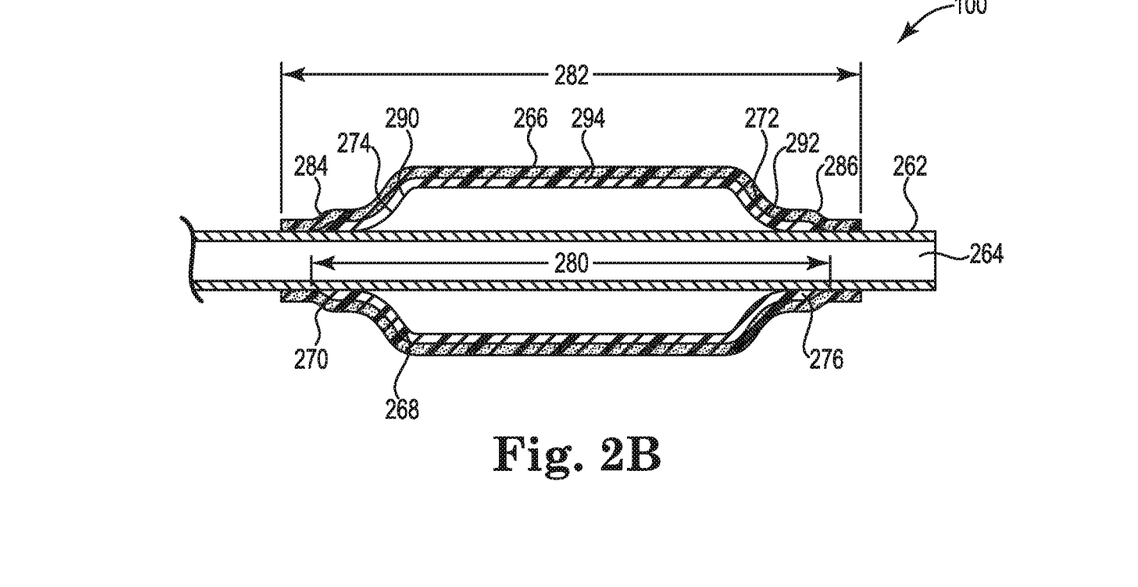

Balloon 268 can comprise, for example a generally tubular shaped balloon capable of inflating within the vasculature of a patient upon pressurization. For example, a biocompatible fluid, such as, for example, water or saline, can be introduced into catheter tube 262, pass through continuous lumen 264 and through an inflation port (not shown) in catheter tube 262 located at the interior of balloon 268, and pressurize balloon 268. As pressure to balloon 268 is increased, the diameter of balloon 268 is also increased.

Balloon 268 can comprise, for example, a non-compliant, generally inelastic balloon. In such embodiments, balloon 268 can comprise a material that is configured to allow balloon 268 to expand to a chosen diameter upon sufficient pressurization and remain at or near the chosen diameter under further pressurization until a burst pressure is reached, such as, for example, nylon, polyethylene, polyethylene terephthalate (PET), polycaprolactam, polyesters, polyethers, polyamides, polyurethanes, polyimides, ABS copolymers, polyester/poly-ether block copolymers, ionomer resins, liquid crystal polymers and rigid rod polymers.

In various embodiments, balloon 268 can comprise a compliant, relatively elastic balloon. In such embodiments, balloon 268 can comprise a material that is configured to allow balloon 268 to continuously increase in diameter as pressure to balloon 268 is increased, such as, for example polyurethanes, latex and elastomeric organosilicone polymers, such as, polysiloxanes. When a distension limit is reached, balloon 268 can rupture.

In yet other embodiments, balloon 268 comprises a semi-compliant balloon. In such embodiments, balloon 268 behaves in a combination of compliant and non-compliant attributes. Although described in connection with compliant and non-compliant embodiments, any material or configuration that allows balloon 268 to inflate in a predictable manner within the body of a patient, including in a combination of compliant and non-compliant behavior, is within the scope of the present disclosure.

Figure 3:
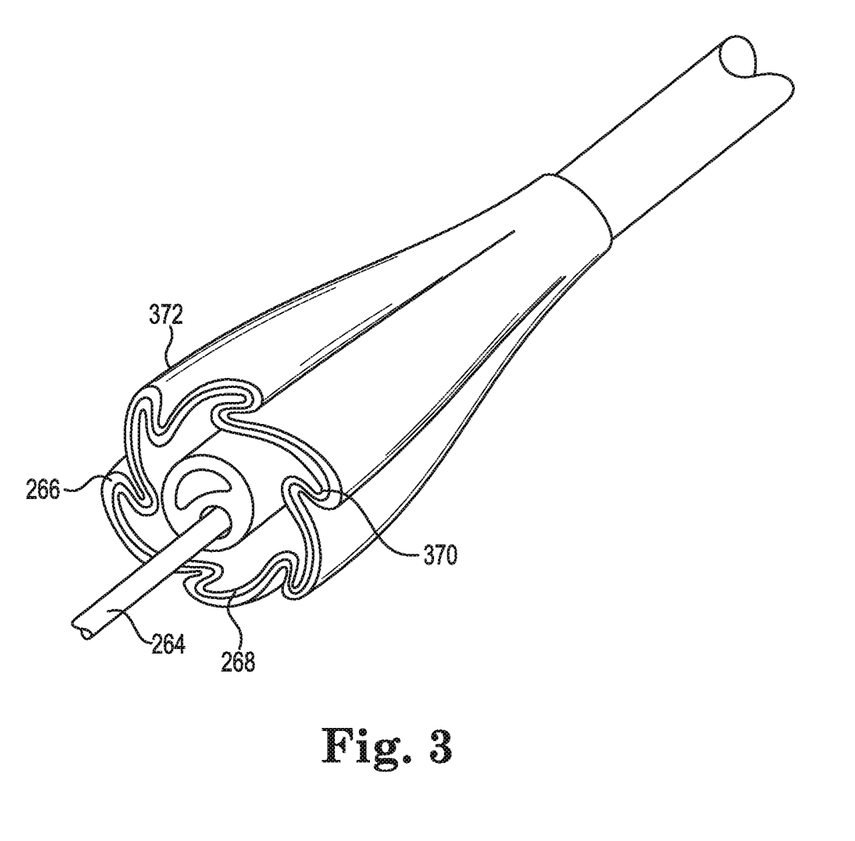
FIG. 3 illustrates a perspective view of a medical device delivery system in accordance with embodiments of the present disclosure.

With reference to FIG. 3, in various embodiments, balloon 268 can comprise a plurality of pleats 370. Pleats 370 can comprise, for example, folds or inflection points in the material of balloon 268 extending generally along at least a portion of longitudinal axis 192. In such embodiments, balloon 268 comprises a generally tubular shape having one or more pleats 370.

In various embodiments, balloon 268 can be coaxially surrounded by cover 266. Cover 266 can comprise an inner surface that can substantially conform to an outer surface of balloon 268, such that both balloon 268 and cover 266 comprise substantially the same shape, including when balloon 268 is deflated. However, in other embodiments, cover 266 can comprise a different shape or configuration from balloon 268.

In various embodiments, cover 266 can comprise a plurality of pleats 372. Similarly to balloon 268, pleats 372 can comprise, for example, folds or inflection points in the material of cover 266 extending generally along at least a portion of the longitudinal axis. In such embodiments, cover 266 comprises a generally tubular shape having two or more pleats 372. In various embodiments, cover 266 comprises the same number of pleats 372 as balloon 268. In various embodiments, along at least a section of or the entire working length of balloon cover 266, the inner surface of balloon cover 266 interfaces with the outer surface of balloon 268 in both the pleated, collapsed configuration and the un-pleated, inflated configuration. In other words, and as shown in FIG. 3, the pleated portions of the cover 266 substantially correspond in their configurations to the corresponding pleated portions of the balloon 268, and the non-pleated portions of the cover 266 substantially correspond in their configurations to the corresponding non-pleated portions of the balloon 268.

Pleats 370 and 372 can be formed in cover 266 and balloon 268 simultaneously. For example, balloon 268 can be coaxially surrounded by cover 266, and pleats 370 and 372 can then be formed in both balloon 268 and cover 266, respectively.

In other embodiments, pleats 372 can be formed in cover 266 after pleats 370 are formed in balloon 268. For example, a pre-pleated balloon 268 can be coaxially surrounded by cover 266. In such embodiments, both cover 266 and pre-pleated balloon 268 can be inflated together to a working pressure, after which cover 266 and balloon 268 are subjected to a mechanical pleat forming process that can form, for example, the same number and configuration of pleats in cover 266 as in pre-pleated balloon 268. While forming pleats 372 in cover 266, both cover 266 and balloon 268 can be deflated and compacted for delivery into the body of a patient. Although described in specific embodiments, any manner of forming pleats in cover 266 is within the scope of the present disclosure.

In yet other embodiments, balloon 268 can comprise a plurality of pleats 370 and cover 266 can comprise no pleats 372. In such embodiments, pleats 370 can be formed in balloon 268, followed by cover 266 being placed coaxially around the outer surface of balloon 268. Although described in connection with specific examples (i.e., balloon 268 and cover 266 both comprising pleats, or only balloon 268 or cover 266 comprising pleats), any configuration in which balloon 268 and/or cover 266 comprises a plurality of pleats is within the scope of the present disclosure.

Cover 266 can comprise, for example, a polymer such as, for example, expanded fluoropolymers, such as, expanded polytetrafluoroethylene (ePTFE), modified (e.g., densified) ePTFE, and expanded copolymers of PTFE. In various embodiments, the polymer can comprise a node and fibril microstructure. In various embodiments, the polymer can be highly fibrillated (i.e., a non-woven web of fused fibrils). Although described in connection with specific polymers, any material or configuration that allows cover 266 to inflate in a predictable manner within the body of a patient is within the scope of the present disclosure.

In various embodiments, cover 266 can comprise multiple layers of a polymeric material. For example, cover 266 can comprise a polymeric material continuously wrapped over a substrate or mandrel to form a generally tubular member. In various embodiments, cover 266 can be constructed with circumferential-, helical-, or axial-orientations of the polymeric material. In such embodiments, the polymeric material can be wrapped generally perpendicular to the longitudinal axis of the mandrel or substrate, i.e., circumferentially wrapped. In other embodiments, the material can be wrapped at an angle between greater than 0 degrees and less than 90 degrees relative to the longitudinal axis of the mandrel or substrate, i.e., helically wrapped. In yet other embodiments, the polymeric material can be wrapped generally parallel to the longitudinal axis of the mandrel or substrate, i.e., axially (or longitudinally) wrapped.

With reference to FIG. 2B, cover 266 can, for example, have a length 282 that is greater than a length 280 of balloon 268. In various embodiments, cover 266 is placed around balloon 268 such that a first cover end 270 and a second cover end 272 extend beyond a first balloon end 274 and second balloon end 276. In such embodiments, a segment 284 of the material of cover 266 positioned at first cover end 270 or second cover end 272 can be compressed along longitudinal axis 192 (i.e., axially compressed). For example, with reference to FIGS. 4A and 4B, segment 284 of the material of cover 266 can be axially compressed (e.g., scrunched) at first cover end 270 and a segment 286 can be axially compressed at second cover end 272.

Figure 4A:
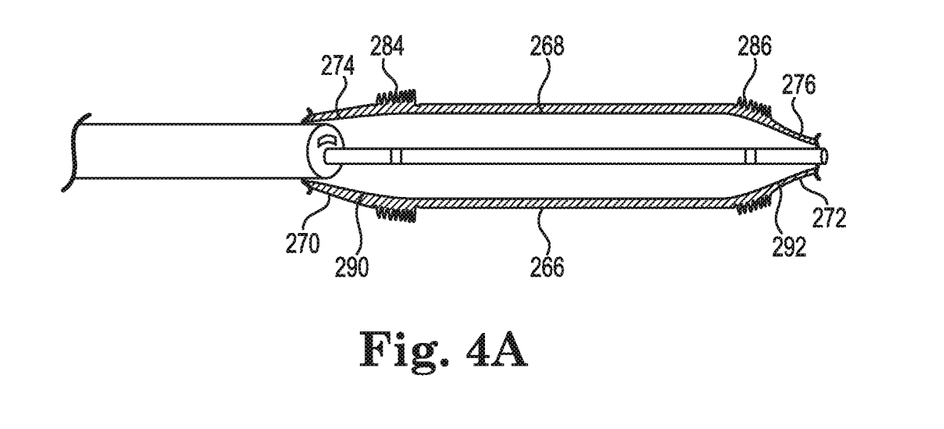
FIGS. 4A and 4B illustrate a cross sectional view of an undeployed balloon and cover and a cross sectional view of a deployed balloon, cover, and endoprosthesis, respectively, in accordance with embodiments of the present disclosure.
Figure 4B:
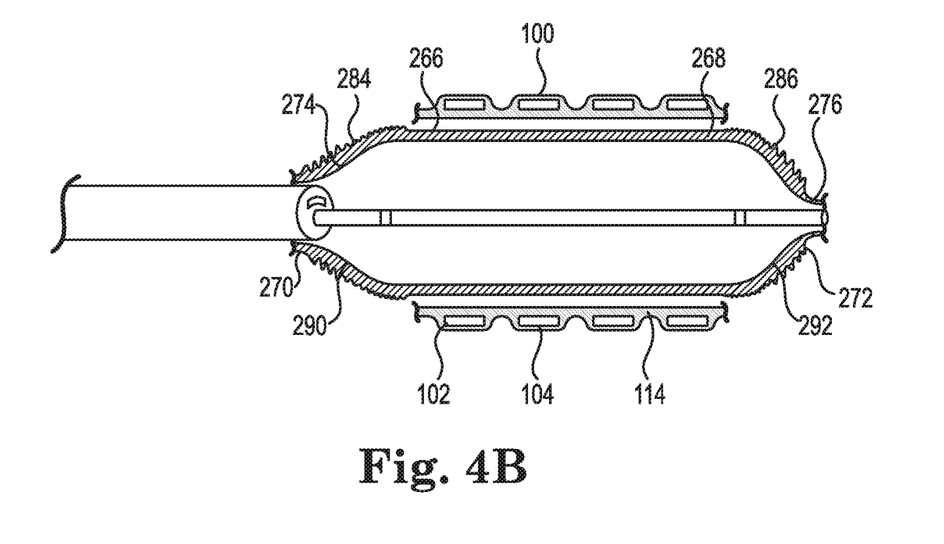

As shown in FIGS. 4A and 4B, segment 284 and/or segment 286 are aligned with a first balloon shoulder 290 and/or a second balloon shoulder 292. In other embodiments, the segments 284 and/or 286 are aligned with different portions of the balloon 268. In FIGS. 4A and 4B, the first balloon shoulder 290 and/or second balloon shoulder 292 are cone-shaped shoulders. Although described with reference to a specific embodiment, any shape of balloon shoulder is within the scope of the present disclosure.

Segment 284 can, for example, be positioned such that it at surrounds at least a portion of first balloon shoulder 290, and segment 284 can be positioned such that it at surrounds at least a portion of second balloon shoulder 292. Providing additional axially compressed (e.g., scrunched) material around balloon shoulders (such as balloon shoulders 290 and 292) can increase the thickness and/or density of cover 266 in the general area of the balloon shoulders. Furthermore, having additional axially compressed material of the cover 266 over the balloon shoulders allows for radial expansion of balloon 268 while limiting axial compression to the balloon during inflation. For example, without having those compressed portions, the shoulders of the balloon will inflate before the body of the balloon and cause axial compression of the balloon and endoprosthesis. But with the axially compressed material, the shoulders of the balloon can expand in a manner that causes less axial compression of the endoprosthesis (e.g., due to the changed angle between the expanded portion of the balloon and the unexpanded or less expanded portion of the balloon) until the pressure within the balloon as a whole is sufficient to more fully expand the cover and the endoprosthesis surrounding the body of the balloon. Further, increased thickness and/or density in the general region of balloon shoulders 290 and 292 can provide additional radial strength to the balloon shoulders to achieve a similar effect.

Figure 5A:
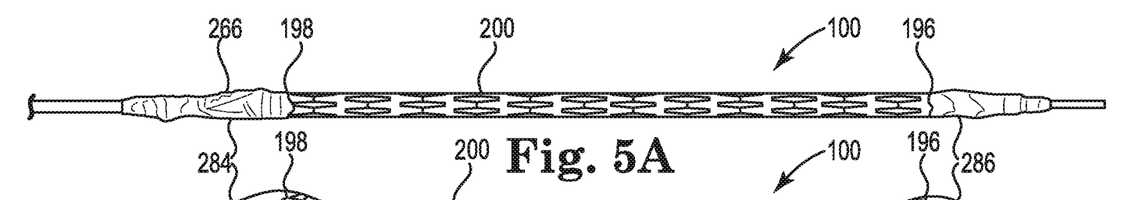
FIGS. 5A-5F illustrate side views of an endoprosthesis delivery system in accordance with embodiments of the present disclosure in various stages of deployment.
Figure 5B:
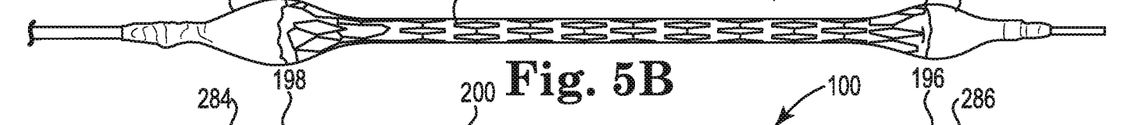
Figure 5C:
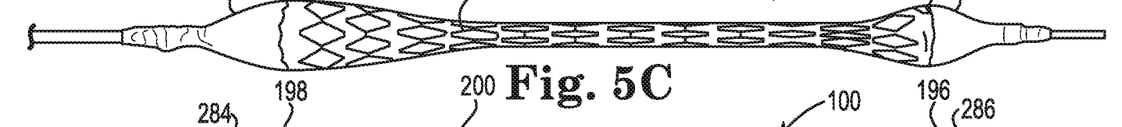
Figure 5D:
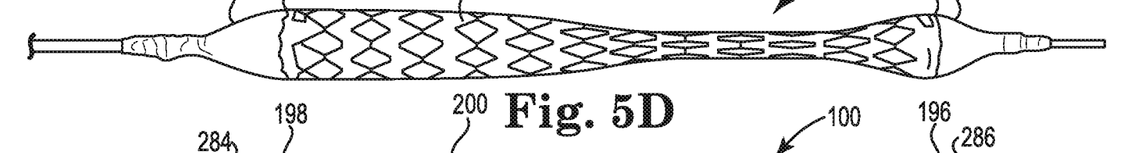
Figure 5E:
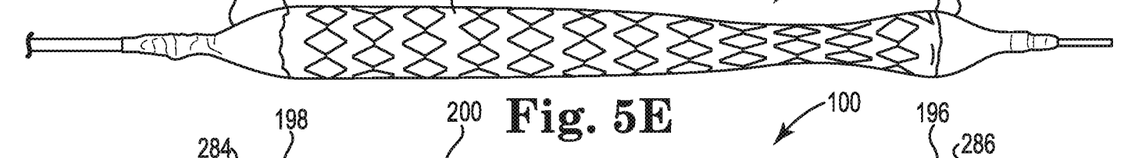
Figure 5F:
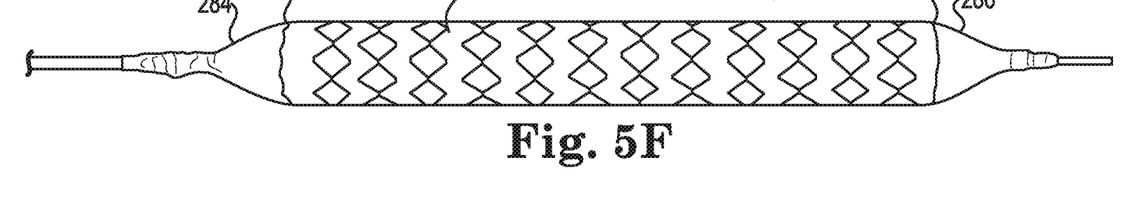

As previously described above, the balloon 268 can be inflated by providing pressurized fluid into balloon 268. FIGS. 5A-5F illustrate one example of the cover 266 restricting expansion of balloon 268 to one desired inflation profile as the balloon 268 is inflated. The intermediate portion 200 of the stent-graft 100 imparts a resistance to expansion of the balloon 268 at the intermediate portion 20 of the stent-graft 100, as well as at, or proximate to, the free ends 196, 198. The cover 266 also imparts a resistance to expansion of the balloon to reduce a difference in an expansion rate of the balloon 268 at the free ends 196, 198 of the stent-graft 100 relative to an expansion rate of the balloon 268 at the intermediate portion 200 of the stent-graft 100 so as to reduce longitudinal compression of the stent-graft 100 as the balloon 268 expands the stent-graft 100 from its undeployed state (FIG. 5A) to its deployed state (FIG. 5F). In some embodiments, the cover 266 acts to equalize the expansion rate of the balloon 268 at the intermediate portion 200 of the stent with the expansion rate of the balloon at, or proximate to the free ends 196, 198 (e.g., proximate or at the shoulders).

For reference, the term "expansion rate" is meant to include the change in diameter vs. pressure, the change in diameter vs. time, or both. For example, equalizing expansion rate of the balloon at the intermediate portion and the free ends includes the balloon achieving substantially the same diameter at the intermediate portion and the free ends at a given pressure (either at substantially the same time, or with some delay between when the intermediate portion vs. the free ends achieve that diameter). Thus, in some embodiments, a reduction in a difference in expansion rates includes a reduction in the difference in pressures required to achieve substantially the same diameter of expansion at the intermediate portion and the free ends, for example.

For example, in some embodiments axially compressed segments 284 and/or 286 are configured to provide additional resistance to the expansion of balloon shoulders 290 and 292, causing a middle portion 294 of balloon 268 to inflate more readily than it would without such segments 284 and 286, which limits the expansion of the balloon shoulders to more closely match the expansion of the middle portion 294 of the balloon 268. Axially compressed segments 284 and/or 286 can also substantially impede inflation of balloon shoulder 290 and/or 292. In various embodiments, this has the effect of controlling the extent of balloon inflation in these regions which, in turn, controls the expansion profile of balloon 268 and/or stent-graft 100.

In various embodiments, the expansion of balloon 268 can be controlled by covered segments 284 and/or 286 in a manner that may reduce undesirable expansion characteristics of stent-graft 100. For example, covered segments 284 and/or 286 may reduce the degree of foreshortening of stent-graft 100 during expansion. In particular, segments 284 and/or 286 may be configured to force the balloon to into a specific inflation profile in which axial forces resulting from inflating balloon shoulders are significantly reduced, for example, due to the diminished angle between the shoulder portions of the balloon and the middle portion of the balloon or the stent-graft. Further, covered segments 284 and/or 286 may reduce or prevent stacking (e.g., reduction of spacing between ringed stent elements 106 during expansion) of stent-graft 100.

With reference to FIGS. 2A and 2B, after balloon 268 is surrounded by cover 266, stent-graft 100 can be loaded on to balloon 268 and cover 266. For example, stent-graft 100 can be positioned to concentrically surround a portion of balloon 268 and cover 266. In various embodiments, once stent-graft 100 is properly positioned around balloon 268 and cover 266, stent-graft 100 is radially compressed to an undeployed diameter 242. For example, stent-graft 100 can be compacted to undeployed diameter 242 to reduce the profile of stent-graft 100 during implantation within a treatment area. Further, stent-graft 100 can be compacted onto balloon 268 and cover 266 so as to resist movement of the stent-graft on balloon 268 prior to deployment.

In various embodiments, upon compaction, stent-graft 100 can imbed itself into cover 266. For example, by imbedding itself into cover 266, stent-graft 100 may exhibit improved stent retention. Such improved stent retention may, for example, assist in maintaining proper positioning of stent-graft 100 relative to cover 266 and/or balloon 268 during deployment to the treatment area of a patient.

Another way to limit any reduction in the length of the endoprosthesis (e.g., as measured between one free end 196 and the opposite free end 198) between its compressed and expanded configurations is by altering the position and/or orientation of the ringed stent elements 104 of a stent member 102. In particular, in some embodiments the position and/or orientation of one or more ringed stent elements 104 of stent member 102 can be altered prior to compaction of stent-graft 100. For example, the distance between two or more adjacent ringed stent element 104 may be reduced prior to compaction of stent-graft 100. For more particular examples, one or more ringed stent elements 104 can be moved so that they are each less than about 1 mm apart from each other or even so that they are in contact with one another (i.e., spaced 0 mm apart from each other).

In other embodiments, the position and/or orientation of ringed stent elements 104 may be altered after compaction of the stent-graft 100. For example, and with reference to FIG. 2A, stent-graft 100 has a length that can be changed by reducing the longitudinal spacing of two or more ringed stent element 104. Reducing the longitudinal spacing between adjacent ringed stent element 104 can, for example, create stored longitudinal length that is recovered when the stent element 104 is expanded into its deployed state. For example, stored longitudinal length may be defined as the length or segment of graft material of intra-ring graft segments 120 axially compressed between adjacent ringed stent elements 104 which is retrieved (i.e., axially expanded) upon expansion and deployment of stent-graft 100. The "undeployed length" of the stent-graft 100 generally refers to the stent-graft 100 in the compressed state prior to delivery and the "deployed length" of the stent-graft 100 generally refers to the stent-graft 100 in the expanded state. In some embodiments, changing the spacing of the ringed stent elements 104 creates a new length that may be referred to as the undeployed length (e.g., length 240 in FIG. 2A).

Stated another way, reducing the spacing between adjacent stent elements 104 can axially compress or scrunch intra-ring graft segments 120. By creating stored length by axial compression, the outside diameter of the stent-graft 100 is not increased. By not increasing the diameter of the device while creating stored length, the transverse-cross section of the device remains minimal and thus does not adversely affect delivery of the stent-graft through the vasculature. At the same time, recovery of the stored length increases the ability of the stent-graft to reduce or offset any loss of length, e.g., due to axial compression forces from inflating the balloon.

Upon delivery of stent-graft 100 to the treatment area of a patient, stent-graft 100 can be deployed. In various embodiments, stent-graft 100 is deployed by inflating balloon 268 to a desired diameter, thereby increasing the diameter of stent-graft 100 from an undeployed diameter 242 to a deployed diameter 146. This process further increases the length of the stent-graft from the undeployed length 240 to a deployed length 148. After balloon 268 is sufficiently inflated, so that deployed diameter 146 is achieved, balloon 268 can be deflated, allowing for removal of catheter assembly 260 from the body of the patient.

Deployed length 148 can, for example, be less than undeployed length 240. For example, deployed length 148 can be about 60% to about 95% of undeployed length 240, and further, about 80% to about 90% of undeployed length 240. Testing has shown that certain embodiments have achieved deployed lengths 148 greater than 99% the undeployed length, thus demonstrating a foreshortening length of less than 1%. The ability of a stent-graft to achieve a high percentage of its undeployed length is also referred to herein as longitudinal efficiency.

Expanding stent-graft 100 from the undeployed configuration to the deployed configuration can also, for example, increase an internal angle of one or more wire frames 106 of ringed stent elements 104. For example, when stent-graft 100 is in the deployed configuration, internal angle 188 of wire frames 106 of ringed stent elements 104 can be between about 70 and 110 degrees, and further, between about 80 and 100 degrees.

Example 1—Bend Radius

Various stent-grafts in accordance with the present disclosure were tested to evaluate their flexibility in the deployed configuration. Specifically, the stent-grafts were tested to determine the bend radius that the stent-graft can accommodate without kinking and can recover its original size and shape after testing. Kinking occurs at the point at which the stent-graft exhibits a diameter reduction of greater than 50%, or where it cannot recover its original size and shape after testing.

The stent-grafts were tested according to ISO25539-2 (2009), section D.5.3.6, method A with the following exceptions: 1) testing was not performed in a tube of the minimum nominal indicated vessel diameters or at maximum indicated vessel diameter, and 2) overlapped condition testing was not performed. The stent-grafts comprise stainless steel ringed stent elements spaced apart at approximately 0.5 mm to 1.5 mm from each other. The stents were approximately 59 mm long. The inner and outer graft elements comprised ePTFE, and the stent-grafts were mounted on a nylon balloon surrounded by an ePTFE cover having scrunched proximal and distal ends. The results of the bend radius testing are summarized below in Table 1.

TABLE 1

|  | Bend Radius (mm) | |
| --- | --- | --- |
| Nominal Diameter (mm) | 5 | 10 |
| Mean | 4 | 7 |
| Maximum | 4 | 8 |
| Minimum | 4 | 6 |
| Sample Size | 10 | 10 |

Example 2—Radial Strength

Various stent-grafts in accordance with the present disclosure were tested to evaluate their radial strength in the deployed configuration. Specifically, the stent-grafts were tested to determine the radial compressive pressure at which the stent-grafts would become irrecoverably deformed.

The stent-grafts were tested according to ISO25539-2: 2009, section D.5.3.4 with the following exceptions: 1) pressure was reported in pounds per square inch, and 2) testing was conducted until a 50% reduction in the nominal device diameter was achieved.

The stent-grafts comprise stainless steel ringed stent elements spaced apart at approximately 0.5 mm to 1.5 mm from each other. The stents were approximately 59 mm long. The inner and outer graft elements comprised ePTFE, and the stent-grafts were mounted on a nylon balloon surrounded by an ePTFE cover having scrunched proximal and distal ends. The results of the radial strength testing are summarized below in Table 2.

TABLE 2

|  | Radial Strength (psi) | |
| --- | --- | --- |
| Nominal Diameter (mm) | 5 | 10 |
| Mean | 18.3 | 11.9 |
| Maximum | 20.9 | 12.6 |
| Minimum | 14.4 | 11.2 |
| Sample Size | 8 | 8 |

While particular embodiments of the present invention have been illustrated and described herein, the present invention should not be limited to such illustrations and descriptions. It should be apparent that changes and modifications may be incorporated and embodied as part of the present invention within the scope of the following claims.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size, and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A medical device, comprising:
an implantable medical device defining a first free end, a second free end, and an intermediate portion between the first and second free ends, the implantable medical device having an undeployed state with an undeployed diameter and an undeployed longitudinal length between the first free end and the second free end and a deployed state with a deployed diameter and a deployed longitudinal length between the first free end and the second free end, the implantable medical device including an expandable support; and
a catheter assembly onto which the implantable medical device is assembled in the undeployed state, the catheter assembly including,
a balloon, and
a cover concentrically surrounding the balloon, the intermediate portion of the implantable medical device imparting a resistance to expansion of the balloon at the intermediate portion of the implantable medical device such that an expansion rate of the balloon at the free ends is at least initially greater than an expansion rate of the balloon at the intermediate portion, and the cover also imparting a resistance to expansion of the balloon to reduce a difference in the expansion rate of the balloon at the free ends of the implantable medical device relative to the expansion rate of the balloon at the intermediate portion of the implantable medical device so as to reduce longitudinal compression of the implantable medical device as the balloon expands the implantable medical device from its undeployed state to its deployed state.

2. The medical device of claim 1, wherein the deployed length of the implantable medical device is at least 85% of the undeployed length of the implantable medical device.

3. The medical device of claim 1, wherein the cover includes reinforcing portions configured to resist inflation of corresponding shoulder portions of the balloon so as to reduce longitudinal compression of the implantable medical device as the balloon expands the implantable medical device from its undeployed state to its deployed state.

4. The medical device of claim 1, wherein the expandable support of the implantable medical device includes a plurality of ring stent elements.

5. The medical device of claim 1, wherein the expandable support graft portion is configured to store longitudinal length of the implantable medical device when the implantable medical device is in the undeployed state.

6. The medical device of claim 1, wherein the expandable support of the implantable medical device comprises an ePTFE membrane.

7. A medical device, comprising:
a implantable medical device defining a first free end, a second free end, and an intermediate portion between the first and second free ends, the implantable medical device having an undeployed state with undeployed longitudinal length between the first free end and the second free end and a deployed state with a deployed longitudinal length between the first free end and the second free end, the implantable medical device including an expandable member; and
a catheter assembly onto which the implantable medical device is assembled in the undeployed state, the catheter assembly including,
a balloon, and
a cover concentrically surrounding the balloon, the intermediate portion of the implantable medical device imparting a resistance to expansion of the balloon at the intermediate portion of the implantable medical device such that an expansion rate of the balloon at the free ends is at least initially greater than an expansion rate of the balloon at the intermediate portion, and the cover also imparting a resistance to expansion of the balloon such that the deployed length of the implantable medical device is at least 85% of the undeployed length of the implantable medical device.

8. The medical device of claim 7, wherein the expandable member of the implantable medical device comprises an ePTFE membrane.

9. A medical device comprising:
an implantable medical device defining a first free end, a second free end, and an intermediate portion between the first and second free ends, including:
an inner ePTFE membrane,
an outer ePTFE membrane, and
a multiplicity of ringed stent elements positioned between the inner ePTFE membrane and the outer ePTFE membrane,
the implantable medical device having an undeployed state with an undeployed diameter and a deployed state with a deployed diameter greater than the undeployed diameter; and
a catheter assembly including a balloon concentrically surrounded by a cover, wherein the balloon is configured to be expanded such that an expansion rate of the balloon at the free ends is at least initially greater than an expansion rate of the balloon at the intermediate portion, the cover including reinforcing portions configured to resist inflation of corresponding shoulder portions of the balloon so as to reduce longitudinal compression of the implantable medical device as the balloon expands the implantable medical device from its undeployed state to its deployed state.

10. The medical device of claim 9, wherein the reinforcing portions of the cover maintain an expansion profile of the balloon that diminishes an amount of radial expansion of the shoulder portions of the balloon relative to a middle portion of the balloon as the balloon is inflated.

11. The medical device of claim 9, wherein the multiplicity of ringed stent elements are configured to store longitudinal length when the implantable medical device is in the undeployed state.

12. The medical device of claim 9, wherein the implantable medical device has an undeployed length in the undeployed state and a deployed length in the deployed state, wherein the deployed length is between 85% and 99% of the undeployed length.

13. The medical device of claim 9, wherein the multiplicity of ringed stent elements comprise interconnected wire frames.

14. The medical device of claim 9, wherein the multiplicity of ringed stent elements comprise a single row of interconnected diamond shaped wire frames.

15. The medical device of claim 9, wherein an apex of a first ringed stent element is out of phase with an adjacent apex of a second ringed stent element along a longitudinal axis.

16. A medical device, comprising:
an implantable medical device defining a first free end, a second free end, and an intermediate portion between the first and second free ends, the implantable medical device having an undeployed state with an undeployed diameter and an undeployed length, and a deployed state with a deployed diameter and a deployed length, the implantable medical device including:
an inner membrane;
an outer membrane; and
a plurality of ringed stent elements positioned between and attached to the inner membrane and the outer membrane; and
a catheter assembly including:
a balloon having a cone-shaped end;
a cover concentrically surrounding the balloon, the cover having a middle portion and a reinforcing portion concentrically surrounding the cone-shaped end of the balloon, the reinforcing portion of the cover having a higher density than a density of the middle portion of the cover in order to expand the balloon such that an expansion rate of the balloon at the free ends is at least initially greater than an expansion rate of the balloon at the intermediate portion, and to maintain an expansion profile that reduces longitudinal compression of the implantable medical device.

17. The medical device of claim 16, wherein a spacing of at least some of the plurality of ringed stent elements when the implantable medical device is in its undeployed state stores longitudinal length that is recovered by the implantable medical device in its deployed state.

18. The medical device of claim 16, wherein the deployed length exhibits less than 1% foreshortening compared to the undeployed length.

19. The medical device of claim 16, wherein the reinforcing portion of the cover has a radial strength that is greater than a radial strength of the middle portion.

20. The medical device of claim 16, wherein the reinforcing portion of the cover restricts expansion of the cone-shaped end of the balloon during inflation of the balloon.

21. The medical device of claim 16, wherein the reinforcing portion of the cover includes an axially compressed portion of the cover.

22. The medical device of claim 16, wherein the reinforcing portion of the cover includes a pleated portion of the cover.

23. The medical device of claim 22, wherein pleatings in the pleated portion of the cover correspond to pleatings in a pleated portion of the balloon.

\* \* \* \* \*